(12) United States Patent
Huang et al.

(10) Patent No.: US 8,658,098 B2
(45) Date of Patent: Feb. 25, 2014

(54) PORTABLE DETECTION SYSTEM FOR ALLERGIC DISEASES

(75) Inventors: I-Yu Huang, Koahsiung (TW);
Yu-Cheng Lin, Kaohsiung (TW);
Chua-Chin Wang, Kaohsiung (TW);
Ying-Chung Chen, Kaohsiung (TW)

(73) Assignee: National Sun Yat-Sen University, Kaohsiung (TW)

( * ) Notice: Subject to any disclaimer, the term of this patent is extended or adjusted under 35 U.S.C. 154(b) by 0 days.

(21) Appl. No.: 13/548,788

(22) Filed: Jul. 13, 2012

(65) Prior Publication Data

US 2013/0309134 A1    Nov. 21, 2013

(30) Foreign Application Priority Data

May 18, 2012   (TW) .............................. 101117933 A (51) Int. Cl.
*G01N 27/00*      (2006.01)

(52) U.S. Cl.
USPC ....... 422/82.01; 422/417; 422/430; 422/68.1; 422/77; 422/513; 422/545; 436/149

(58) Field of Classification Search
USPC .............. 422/400, 417, 430, 68.1, 77, 82.01, 422/502, 513, 545; 436/149
See application file for complete search history.

(56) References Cited

U.S. PATENT DOCUMENTS

| 7,999,440 | B2 * | 8/2011 | Miller et al. | ................... 310/324 |
| 2005/0065446 | A1 * | 3/2005 | Talton | ............................. 600/529 |
| 2008/0254486 | A1 * | 10/2008 | Hayward et al. | ............... 435/7.8 |

\* cited by examiner

*Primary Examiner* — Lyle Alexander
(74) *Attorney, Agent, or Firm* — Jackson IPG PLLC (57) ABSTRACT

A portable detection system for allergic diseases includes a filtration-based inspection module and a reader module. The filtration-based inspection module includes an FPW sensor and a liquid sample filtration apparatus, wherein the liquid sample filtration apparatus includes an injection opening, a passage module, a filtering membrane and a gathering aperture. The injection opening is in communication with the gathering aperture. The FPW sensor comprises a frame body, a carrier and a sensing chip having an accommodating slot in communication with the gathering aperture. The carrier comprises a plurality of conductive terminals, and the conductive terminals are electrically connected with the sensing chip. The reader module comprises a connection slot capable of being inserted by the conductive terminals of the carrier.

18 Claims, 7 Drawing Sheets

PORTABLE DETECTION SYSTEM FOR ALLERGIC DISEASES

FIELD OF THE INVENTION

The present invention is generally related to a portable detection system, which particularly relates to the portable detection system for allergic diseases.

BACKGROUND OF THE INVENTION

ELISA (Enzyme-linked immunosorbent assay) analysis is one of the primary detection methods for immunoglobulin concentration. However, in ELISA analysis procedure, a sample must undergo preprocess of heating and centrifugation, which results in reduction of solubility, denatured globulin and loss of antigenicity. Accordingly, mentioned heating process appears to substantially compromise the accuracy of immunoglobulin concentration. In addition, the amount of reagent applied in conventional ELISA analyzer is huge, and the examination expenses for patient burden are relatively expensive. Besides, a completed examination procedure takes 7 to 10 days so that a patient suffered from allergic disease can not proceed with immediate detection.

SUMMARY

The primary object of the present invention is to provide a portable detection system for allergic diseases including a filtration-based inspection module and a reader module. The filtration-based inspection module includes an FPW sensor and a liquid sample filtration apparatus, wherein the liquid sample filtration apparatus includes an injection opening, a passage module, a filtering membrane and a gathering aperture. The injection opening is in communication with the gathering aperture. The FPW sensor comprises a frame body, a carrier and a sensing chip having an accommodating slot in communication with the gathering aperture. The carrier is coupled to the frame body, and the sensor is disposed at the carrier. The carrier comprises a plurality of conductive terminals, and the conductive terminals are electrically connected with the sensing chip. The reader module comprises a connection slot capable of being inserted by the conductive terminals of the carrier.

In this invention, the filtration-based inspection module enables to separate blood serum from whole blood via the liquid sample filtration apparatus. Through serum detection, the FPW sensor enables to output a first AC signal contained with information of immunoglobulin concentration for blood serum and a second AC signal. Eventually, immunoglobulin concentration in certain blood serum is obtainable and displayable from the reader module via the first AC signal and the second AC signal.

The portable detection system for allergic diseases possesses feature of rapid detection for immunoglobulin concentration in human serum. A patient suffered from allergic disease can utilize mentioned detection system to proceed with immediate detection. Furthermore, in contrast with conventional blood analyzer, the portable detection system for allergic diseases can be provided with characteristics of smaller size, less sample volume and less detection time.

DETAILED DESCRIPTION OF THE INVENTION

Figure 1:
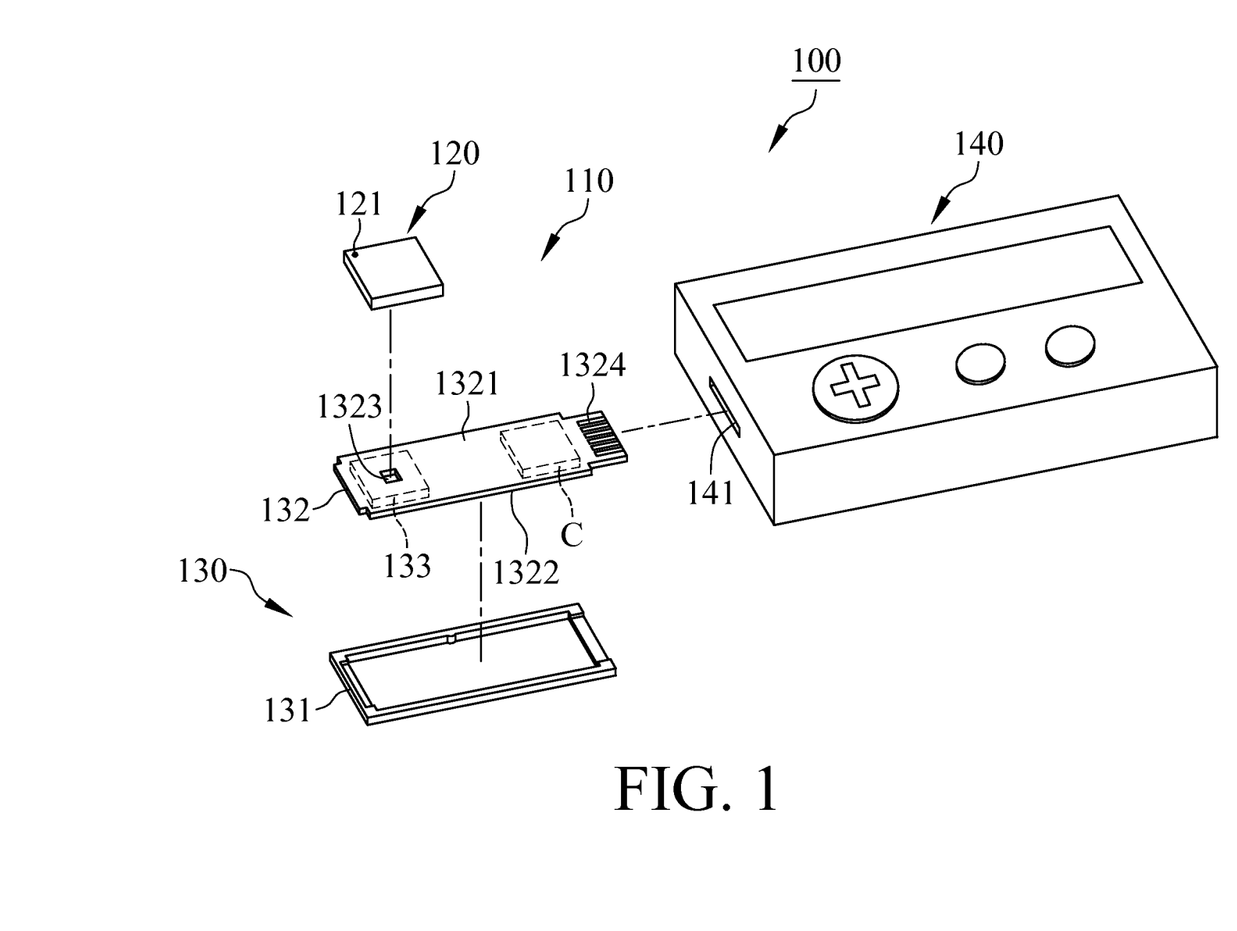
FIG. 1 is a perspective exploded diagram illustrating a portable detection system for allergic diseases in accordance with a preferred embodiment of the present invention.
Figure 2:
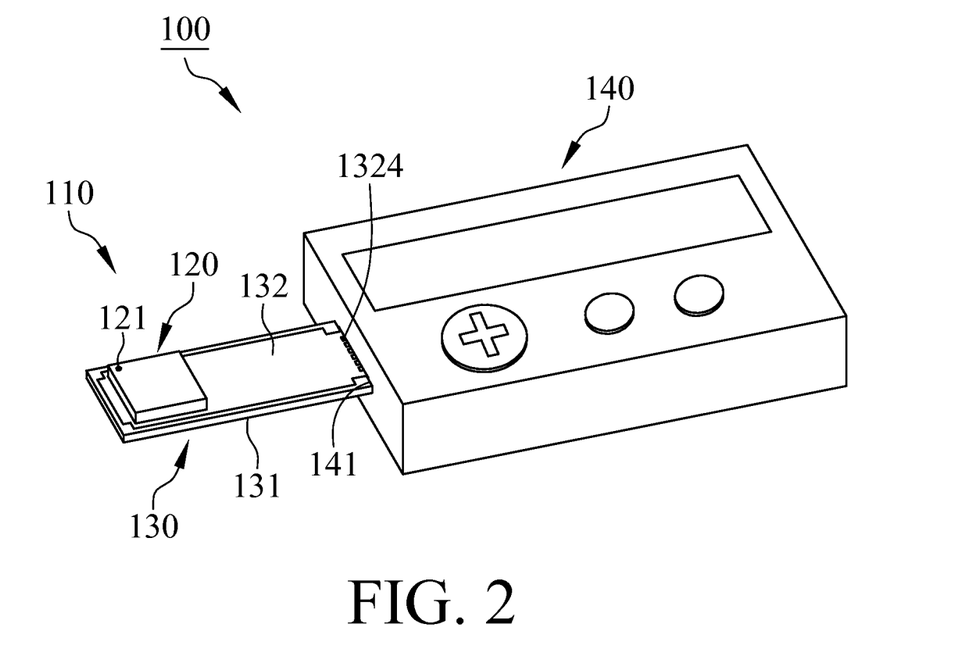
FIG. 2 is a perspective assembly diagram illustrating a portable detection system for allergic diseases in accordance with a preferred embodiment of the present invention.
Figure 3:
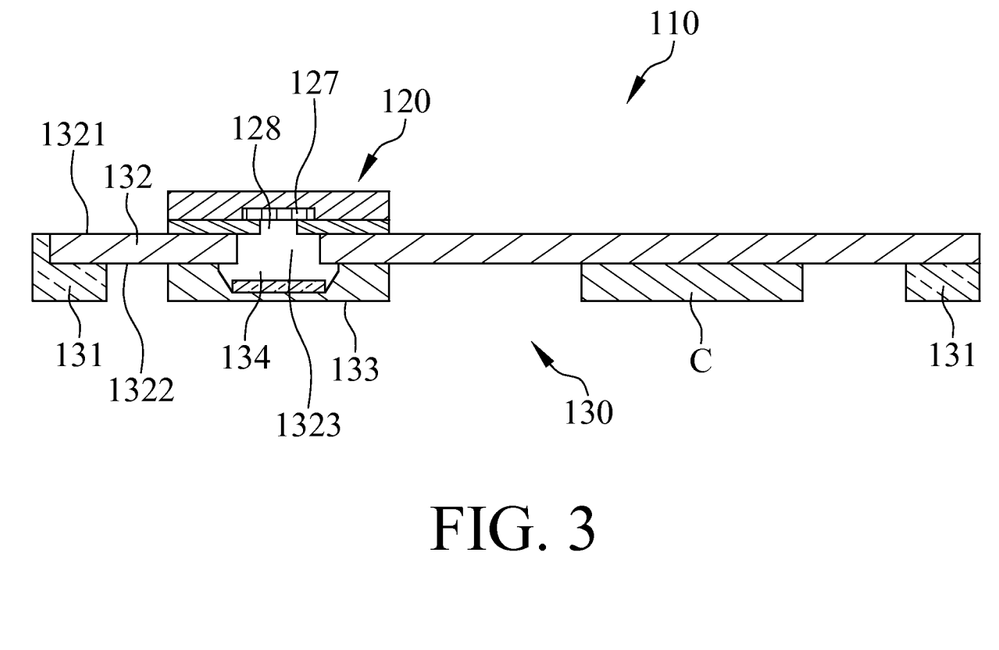
FIG. 3 is a lateral section view illustrating a filtration-based inspection module of a portable detection system for allergic diseases in accordance with a preferred embodiment of the present invention.
Figure 4:
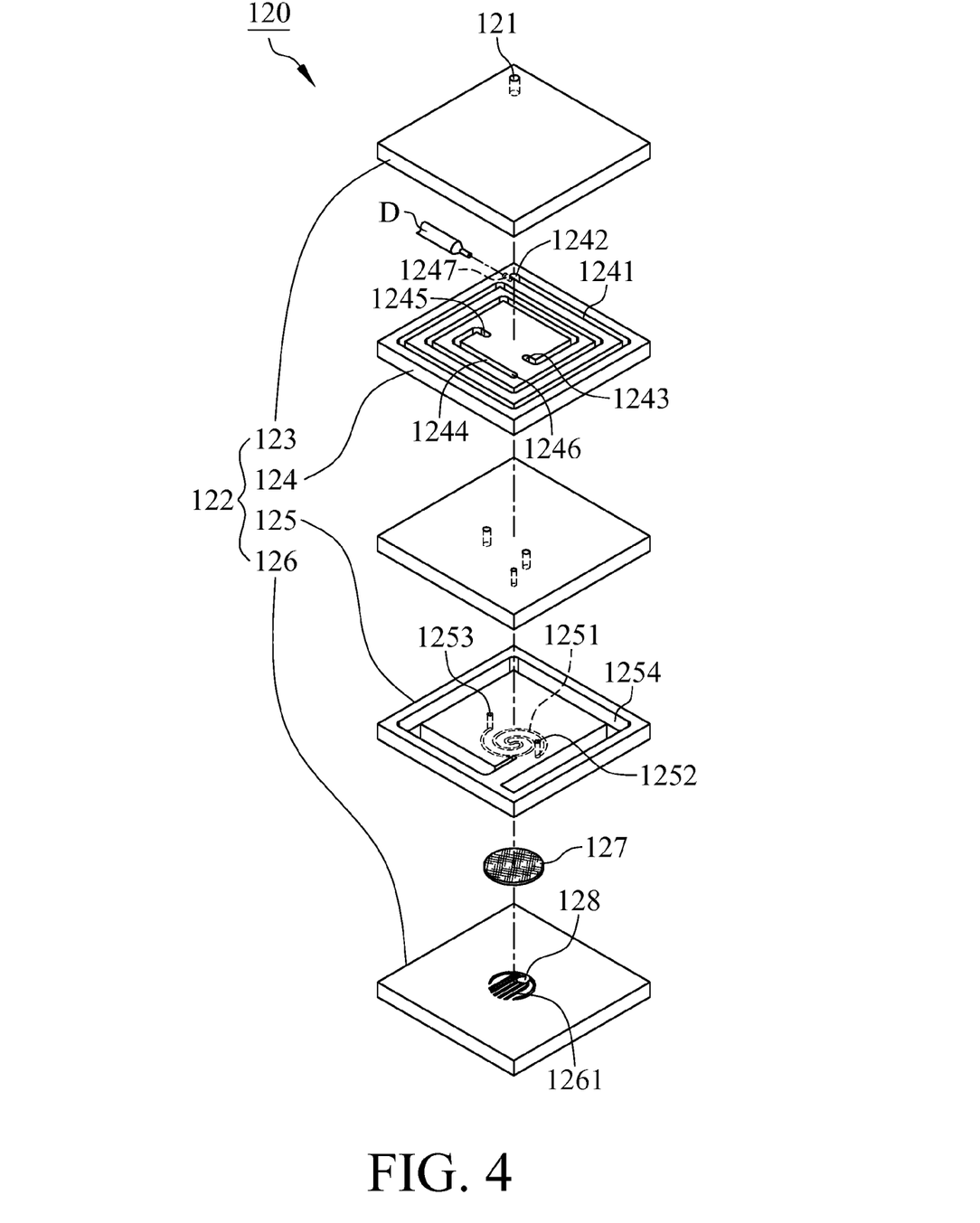
FIG. 4 is a perspective exploded diagram illustrating a liquid sample filtration apparatus of a portable detection system for allergic diseases with a preferred embodiment of the present invention.
Figure 5A:
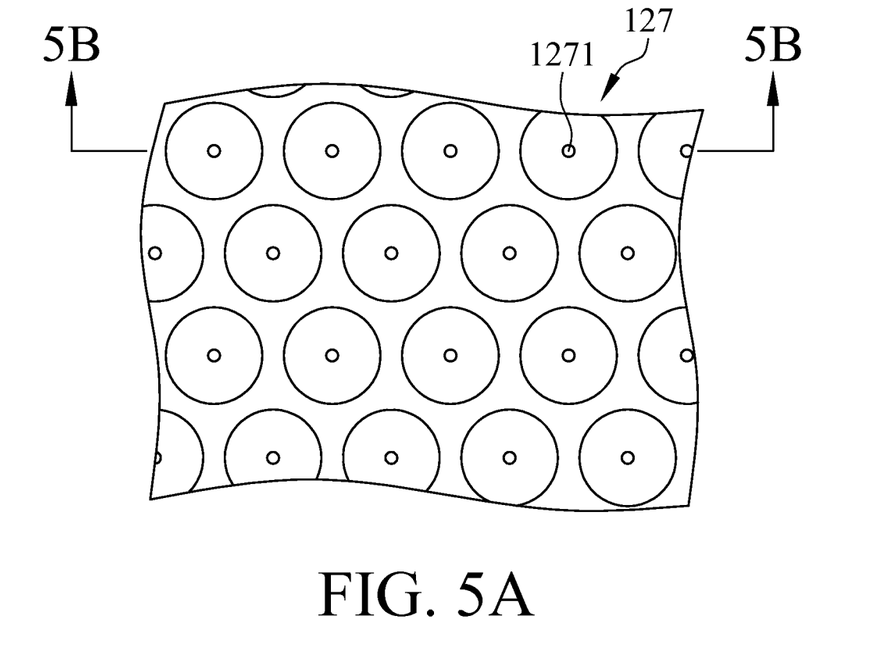
FIG. 5A is a bottom view illustrating a filtering membrane of a portable detection system for allergic diseases in accordance with a preferred embodiment of the present invention.
Figure 5B:
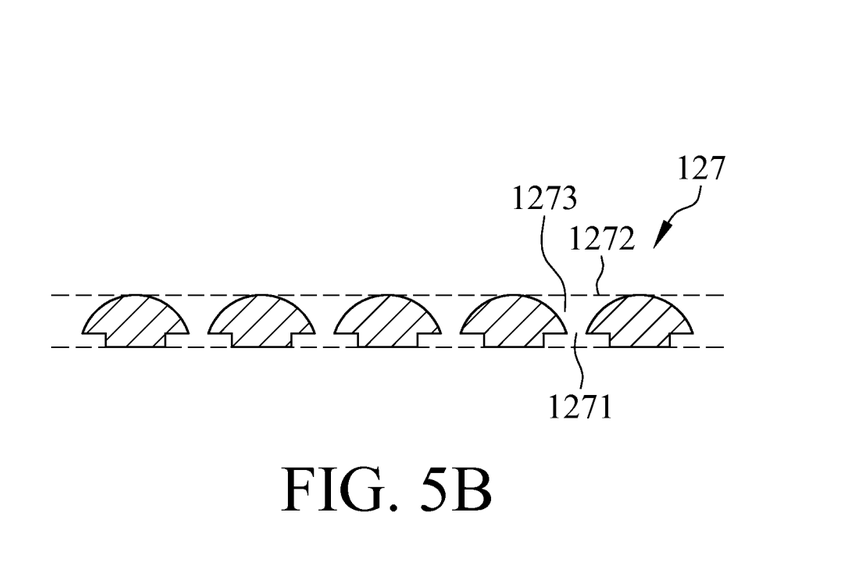
FIG. 5B is a section view taken along line 5B-5B of FIG. 5A.

With reference to FIGS. 1 and 2, a portable detection system for allergic diseases 100 in accordance with a preferred embodiment of the present invention utilizes for immunoglobulin concentration detection of a liquid sample. The portable detection system for allergic diseases 100 includes a filtration-based inspection module 110 and a reader module 140, wherein the filtration-based inspection module 110 includes a liquid sample filtration apparatus 120 and an FPW (flexural plate wave) sensor 130, and the liquid sample filtration apparatus 120 is installed at the FPW sensor 130. Referring to FIGS. 4, 5A and 5B, the liquid sample filtration apparatus 120 includes an injection opening 121, a passage module 122, a filtering membrane 127 and a gathering aperture 128, and the injection opening 121 is in communication with the gathering aperture 128. With reference to FIGS. 5A and 5B again, in this embodiment, the filtering membrane 127 comprises a plurality of pores 1271, and the injection opening 121 is in communication with the gathering aperture 128 via the pores 1271. With reference to FIGS. 1 and 3, the FPW sensor 130 comprises a frame body 131, a carrier 132 coupled to the frame body 131, a sensing chip 133 and a comparison chip C, wherein the carrier 132 comprises a top surface 1321, a bottom surface 1322, an opening 1323 and a plurality of conductive terminals 1324, the sensing chip 133 and the comparison chip C are disposed at the bottom surface 1322 of the carrier 132, the liquid sample filtration apparatus 120 is disposed at the top surface 1321, the top surface 1321 is in communication with the bottom surface 1322 via the opening 1323, and the conductive terminals 1324 are electrically connected with the sensing chip 133 and the comparison chip C. The gathering aperture 128 is in communication with an accommodating slot 134 of the sensing chip 133, preferably, the opening 1323 is in communication with the accommodating slot 134 and the gathering aperture 128. The reader module 140 comprises a guiding slot 141, the connection terminals 1324 of the FPW sensor 130 are inserted into the guiding slot 141.

Figure 6:
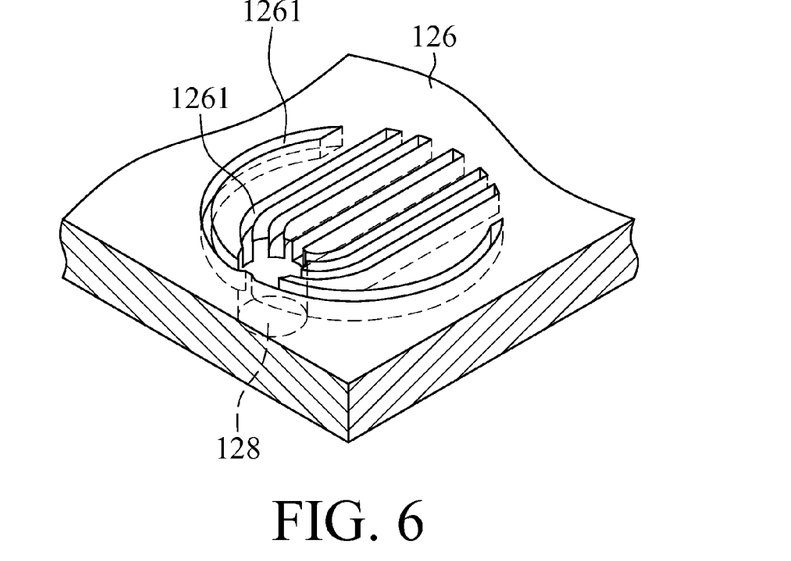
FIG. 6 is a perspective diagram illustrating a collection layer of a liquid sample filtration apparatus of a portable detection system for allergic diseases with a preferred embodiment of the present invention.
Figure 7:
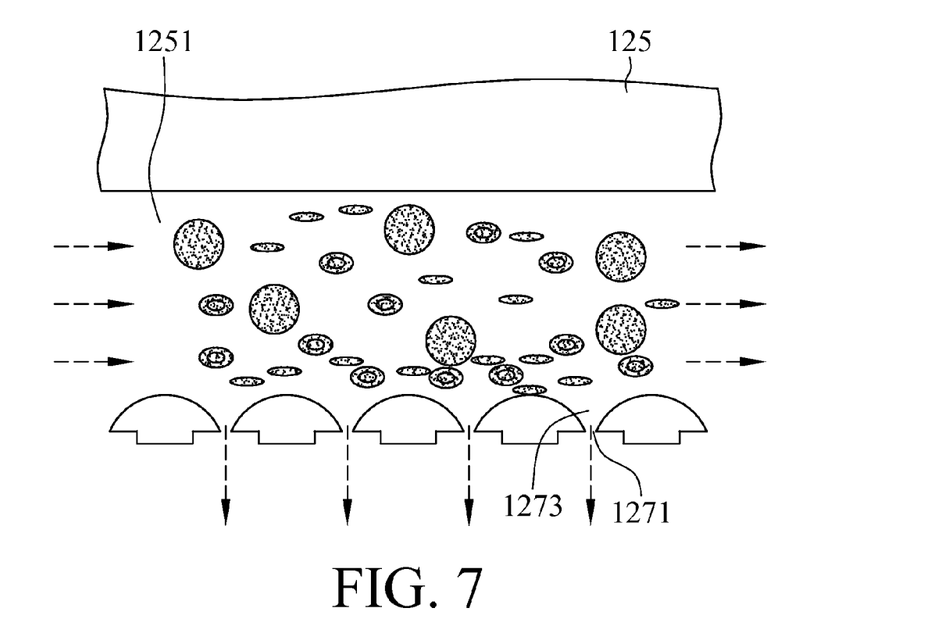
FIG. 7 is a diagram illustrating a filtering membrane of a liquid sample filtration apparatus of a portable detection system for allergic diseases under process of whole blood separation.

With reference to FIGS. 5A, 5B and 7, the filtering membrane 127 further comprises a surface 1272, a plurality of guidance slots 1273 are recessed from the surface 1272, and each of the pores 1271 is formed at each of the guidance slots 1273. In this embodiment, the liquid sample can be a whole blood, when the whole blood flows through the filtering membrane 127, the guidance slots 1273 enables to guide serums of the whole blood into the pores 1271 of the filtering membrane 127 to increase the filtration speed of the liquid sample filtration apparatus 120. Referring to FIG. 4 again, the passage module 122 includes a lid 123, a sample-accommodating layer 124, a filtration layer 125 and a collection layer 126, wherein the lid 123 covers the sample-accommodating layer 124, the injection opening 121 is formed at the lid 123, and the sample-accommodating layer 124 is disposed on top of the filtration layer 125. The sample-accommodating layer 124 comprises a first passage 1241 having a first inlet 1242 and a first outlet 1243, the injection opening 121 corresponds to and communicates with the first inlet 1242. Besides, the filtration layer 125 is disposed on top of the collection layer 126 and comprises a second passage 1251, wherein the filtering membrane 127 is located between the second passage 1251 and the gathering aperture 128, and the pores 1271 of the filtering membrane 127 are in communication with the second passage 1251. In this embodiment, the second passage 1251 can be a vortex-shaped passage. The second passage 1251 comprises a second inlet 1252, and the first outlet 1243 of the first passage 1241 corresponds to and communicates with the second inlet 1252 of the second passage 1251. Referring to FIG. 6, the gathering aperture 128 is formed at the collection layer 126. The collection layer 126 comprises a plurality of third passages 1261 in communication with the gathering aperture 128 and the pores 1271 of the filtering membrane 127. In this embodiment, the third passages 1261 can be claw-shaped, fork-shaped, broom-shaped, comb-shaped or fence-shaped passages.

Referring to FIG. 4, the filtration layer 125 further comprises a storage slot 1254, the second passage 1251 of the filtration layer 125 further comprises a second outlet 1253, and the sample-accommodating layer 124 further comprises a fourth passage 1244. The second outlet 1253 is in communication with the fourth passage 1244, preferably, the fourth passage 1244 comprises a third inlet 1245 and a third outlet 1246, the second outlet 1253 corresponds to and communicates with the third inlet 1245, and the third outlet 1246 communicates with the storage slot 1254. In this embodiment, the material of the liquid sample filtration apparatus 120 can be selected from one of Polymethylmethacrylate (PMMA), Polydimethylsiloxane (PDMS), epoxy, metal or glass.

Figure 8:
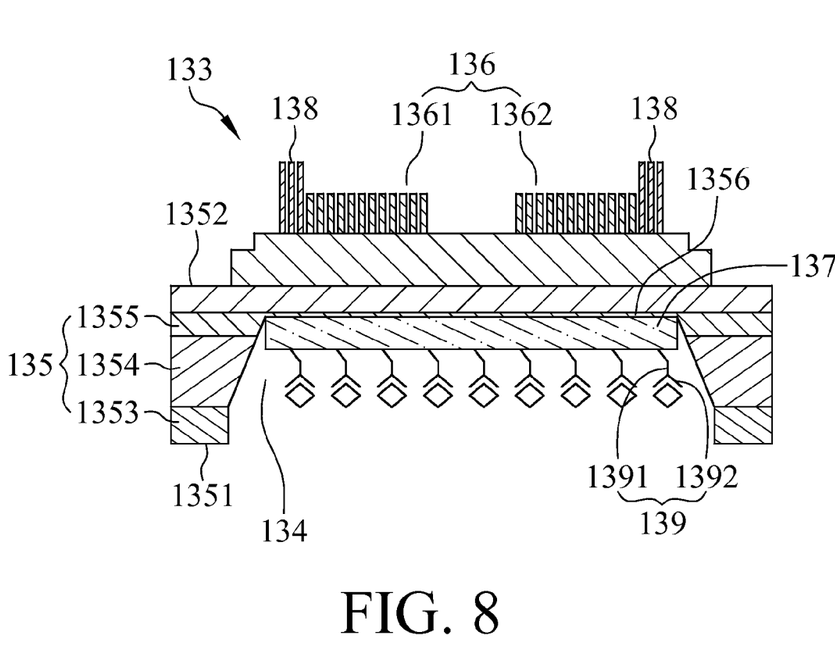
FIG. 8 is a lateral section view illustrating an FPW sensor of a liquid sample filtration apparatus of a portable detection system for allergic diseases.

With reference to FIG. 8, in this embodiment, the sensing chip 133 includes a substrate 135, an inter-digital transducer 136, a metal layer 137, a gate electrode 138 and a self-assembled single molecule layer 139, wherein the substrate 135 comprises a first side 1351, a second side 1352, a separation layer 1353, a P-type silicon layer 1354 and an N-type epitaxy silicon layer 1355. The P-type silicon layer 1354 is disposed on the separation layer 1353, the N-type epitaxy silicon layer 1355 is disposed on the P-type silicon layer 1354, the accommodating slot 134 penetrates through the separation layer 1353 and the P-type silicon layer 1354, the accommodating slot 134 reveals the N-type epitaxy silicon layer 1355, and an N-type epitaxy silicon membrane 1356 is formed on the N-type epitaxy silicon layer 1355. The inter-digital transducer 136 is disposed at the second side 1352 of the substrate 135, the metal layer 137 is disposed on the N-type epitaxy silicon membrane 1356, and the gate electrode 138 is disposed at two sides of the inter-digital transducer 136. The self-assembled single molecule layer 139 comprises a plurality of self-assembled single molecules 1391 and a plurality of immunoglobulin E antibodies 1392, wherein each of the self-assembled single molecules 1391 comprises an aldehyde group (not shown in Figs.) alternately disposed on the metal layer 137, each of the immunoglobulin E antibodies 1392 comprises a front end (not shown in Figs.) and a coupling end (not shown in FIGS.), the front end is connected with the aldehyde group, and the coupled end is coupled to an immunoglobulin E antigen of each of the serums. In this embodiment, the thickness of the N-type epitaxy silicon membrane 1356 of the N-type epitaxy silicon layer 1355 is not larger than 3 micro meters. Owning to the reason that the thickness of the N-type epitaxy silicon membrane 1356 is controllable less than 3 micro meters, the measurable center frequency of the FPW sensor 130 can be reached to 10 MHz. Further, the thickness of the gate electrode 138 is 3 micro meters. The gate electrode 138 enables to reduce the transmission loss of flexural plate wave. In this embodiment, the transmission loss is less than 20 dB. The thickness of the N-type epitaxy silicon layer 1355 is 20 micro meters.

With reference to FIGS. 4 and 8 again, the examination procedure of the portable detection system for allergic diseases 100 describes as below: first, referring to FIG. 4, injecting the whole blood into the injection opening 121 of the liquid sample filtration apparatus 120 so as to make the whole blood flowable in the first passage 1241. In this embodiment, the portable detection system for allergic diseases 100 further comprises a driving device D, the sample-accommodating layer 124 further comprises a penetration hole 1247, and the driving device D is coupled to the penetration hole 1247. The driving device D is utilized for compressing the air inside the penetration hole 1247 to push forward the whole blood flowed in the first passage 1241. Preferably, the driving device D can be a piezoelectric micro pump; next, the whole blood flows from the first passage 1241 to the second passage 1251. For the reason that the filtering membrane 127 is located right beneath the second passage 1251, the serums of the whole blood can pass through the pores 1271 of the filtering membrane 127 and flow into the third passages 1261, and the serums are then flowed into the accommodating slot 134 of the sensing chip 133 through the gathering aperture 128 and the opening 1323 of the carrier 132. Comparatively, the remains in the whole blood, such as suspended substances, micro particles and solid substances, can not pass through the pores 1271 owning to the reason that particle diameter of those remains is larger than bore diameter of the pores 1271, as indicated in FIG. 7. Therefore, mentioned remains of the whole blood merely flow from the second outlet 1253 of the second passage 1251 to the fourth passage 1244. Eventually, the remains flow from the fourth passage 1244 to the storage slot 1254 for waste liquid storage. Referring to FIGS. 3 and 8, the serums drop into the accommodating slot 134 of the sensing chip 133, and an immunoglobulin E antigen of each of the serums is coupled to the coupling end (not shown in Figs.) of each of the immunoglobulin E antibodies 1392 resulting changes in characteristic. In this embodiment, the inter-digital transducer 136 comprises a set of input transducer 1361 and a set of output transducer 1362, the inter-digital transducer 136 converts an AC signal that is added in the input transducer 1361 into a flexural plate wave by means of converse piezoelectric effect. Then, mentioned flexural plate wave is transmitted and contacts the output transducer 1362 to be converted into a first AC signal by means of direct piezoelectric effect. Meanwhile, the comparison chip C outputs a second AC signal simultaneously, wherein the second AC signal is a reference signal utilized for comparison with the first AC signal. With reference to FIG. 2, the first AC signal and the second AC signal are transmitted to the reader module 140 through the conductive terminals 1324 that is inserted into the reader module 140. A frequency difference value can be calculated from the frequency of the first AC signal and the frequency of the second AC signal, and the immunoglobulin concentration of the serums is obtainable from the reader module 140 via the frequency difference value. In this embodiment, the reader module 140 enables to display the data of the immunoglobulin concentration for certain serums.

In present invention, the filtration-based inspection module 110 utilizes the filtering membrane 127 of the liquid sample filtration apparatus 120 to separate the serums from the whole blood. Through serums detection of the FPW sensor 130, the FPW sensor 130 enables to output the second AC signal and the first AC signal contained with information of immunoglobulin concentration for certain serums. A frequency difference is calculated by the reader module 140 from the frequency of the first AC signal and the frequency of the second AC signal, and the immunoglobulin concentration of the serums is obtainable via the frequency difference value. The portable detection system for allergic diseases 100 enables to proceed with immediate detection for the immunoglobulin concentration of human serums. A patient suffered from allergic diseases can apply mentioned detection system in preliminary diagnosis of allergic diseases. Besides, the filtration-based inspection module 110 adopts a batch process of MEMS and IC. Therefore, the filtration-based inspection module 110 is effectively integrated as a system chip. Furthermore, in contrast with conventional blood analyzer, the portable detection system for allergic diseases 100 can be provided with characteristics of smaller size, less sample volume and less detection time.

While this invention has been particularly illustrated and described in detail with respect to the preferred embodiments thereof, it will be clearly understood by those skilled in the art that it is not limited to the specific features and describes and various modifications and changes in form and details may be made without departing from the spirit and scope of this invention.

What is claimed is:

1. A portable detection system for allergic diseases including a filtration-based inspection module including:
    a liquid sample filtration apparatus including an injection opening, a passage module, a filtering membrane and a gathering aperture in communication with the injection opening; and
    a flexural plate wave (FPW) sensor comprising:
        a frame body,
        a carrier comprising a to surface wherein the liquid sample filtration apparatus is disposed at the top surface, a bottom surface and an opening wherein the to surface is in communication with the bottom surface via the opening, and
        a first FPW sensing chip disposed at the bottom surface and having an accommodating slot and comprising;
            a substrate having a first side and a second side,
            a separation layer,
            a P-type silicon layer disposed on the separation layer,
            an N-type epitaxy silicon layer disposed on the P-type silicon layer, wherein the accommodating slot penetrates through the separation layer and the P-type silicon layer and reveals the N-type epitaxy silicon layer,
            an N-type epitaxy silicon membrane formed from the N-type epitaxy silicon layer;
            a transducer disposed at the second side of the substrate;
            a metal layer disposed at the N-type epitaxy silicon membrane;
            a gate electrode disposed at two sides of the transducer; and
            a self-assembled single molecule layer having a plurality of self-assembled single molecules and a plurality of immunoglobulin E antibodies, wherein each of the self-assembled single molecules comprises an aldehyde group, each of the aldehyde groups alternately disposed on the metal layer and each of the immunoglobulin E antibodies comprises a front end and a coupling end, wherein the front end is connected with a corresponding aldehyde group, and the coupling end is coupled to a corresponding immunoglobulin E antigen, wherein the carrier is coupled to the frame body and comprises a plurality of conductive terminals, the sensing chip is disposed at the carrier, the conductive terminals are electrically connected with the sensing chip, the gathering aperture is in communication with the accommodating slot of the sensing chip; and
    a reader module having a guiding slot, wherein the connection terminals of the filtration-based inspection module are inserted into the guiding slot and wherein the opening is in communication with the accommodating slot and the gathering aperture.

2. The portable detection system for allergic diseases in accordance with claim 1, wherein the thickness of the N-type epitaxy silicon membrane of the N-type epitaxy silicon layer is not larger than 3 micro meters.

3. The portable detection system for allergic diseases in accordance with claim 1, wherein the thickness of the gate electrode is 3 micro meters.

4. The portable detection system for allergic diseases in accordance with claim 1, wherein the thickness of the N-type epitaxy silicon layer is 20 micro meters.

5. The portable detection system for allergic diseases in accordance with claim 1, wherein the FPW sensor further comprises a second FPW comparison chip, wherein the conductive terminals of the carrier are electrically connected with the second FPW comparison chip.

6. The portable detection system for allergic diseases in accordance with claim 1, wherein the filtering membrane comprises a plurality of pores in communication with the gathering aperture.

7. The portable detection system for allergic diseases in accordance with claim 6, wherein the filtering membrane further comprises a surface, a plurality of guidance slots are recessed from the surface, and each of the pores is formed at each of the guidance slots.

8. The portable detection system for allergic diseases in accordance with claim 6, wherein the passage module includes a filtration layer having a second passage, the filtering membrane is located between the second passage and the gathering aperture, and the pores are in communication with the second passage.

9. The portable detection system for allergic diseases in accordance with claim 8, wherein the second passage is a vortex-shaped passage.

10. The portable detection system for allergic diseases in accordance with claim 8, wherein the passage module further includes a sample-accommodating layer disposed on top of the filtration layer, the sample-accommodating slot comprises a first passage in communication with the second passage of the filtration layer.

11. The portable detection system for allergic diseases in accordance with claim 10, wherein the second passage comprises a second inlet, the first passage comprises a first outlet, the second inlet corresponds to and communicates with the first outlet.

12. The portable detection system for allergic diseases in accordance with claim 11, wherein the passage module further includes a lid covering the sample-accommodating layer, the injection opening is formed at the lid, the first passage comprises a first inlet, and the injection opening corresponds to and communicates with the first inlet.

13. The portable detection system for allergic diseases in accordance with claim 10 further comprises a driving device configured to compress air, the sample-accommodating layer comprises a penetration hole, and the driving device is configured to be coupled to the penetration hole.

14. The portable detection system for allergic diseases in accordance with claim 8, wherein the passage module further includes a collection layer having a plurality of third passages, the filtration layer is disposed on top of the collection layer, the gathering aperture is formed at the collection layer, and the third passages are in communication with the gathering aperture and the pores.

15. The portable detection system for allergic diseases in accordance with claim 14, wherein the third passages comprises one of claw-shaped, fork-shaped, broom-shaped, comb-shaped or fence-shaped passages.

16. The portable detection system for allergic diseases in accordance with claim 8, wherein the filtration layer further comprises a storage slot, the second passage is in communication with the storage slot.

17. The portable detection system for allergic diseases in accordance with claim 16, wherein second passage comprises a second outlet, the sample-accommodating layer further comprises a fourth passage, and the second outlet is in communication with the fourth passage.

18. The portable detection system for allergic diseases in accordance with claim 17, wherein the fourth passage comprises a third inlet and a third outlet, the second outlet corresponds to and communicates with the third inlet, and the third outlet is in communication with the storage slot.

* * * * *